(12) United States Patent
Morad et al.

(10) Patent No.: US 11,911,253 B1
(45) Date of Patent: Feb. 27, 2024

(54) BULK LOADING FEMININE HYGIENE PRODUCT DISPENSER

(71) Applicant: The Tranzonic Companies, Cleveland, OH (US)

(72) Inventors: Fred I. Morad, Toluca Lake, CA (US); Robert A. Acosta, Norwalk, CA (US); Arbi Petrosian, Glendale, CA (US)

(73) Assignee: The Tranzonic Companies, Cleveland, OH (US)

( * ) Notice: Subject to any disclaimer, the term of this patent is extended or adjusted under 35 U.S.C. 154(b) by 0 days.

(21) Appl. No.: 18/495,087

(22) Filed: Oct. 26, 2023

(51) Int. Cl.
  *G07F 11/16* (2006.01)
  *A61F 15/00* (2006.01)

(52) U.S. Cl.
  CPC ............ *A61F 15/003* (2013.01); *G07F 11/16* (2013.01)

(58) Field of Classification Search
  CPC ............................. A61F 15/003; G07F 11/16
  See application file for complete search history.

(56) References Cited

U.S. PATENT DOCUMENTS

| 11,141,328 B1 | 10/2021 | Morad et al. | |
| 2011/0101020 A1* | 5/2011 | Granger | A47K 10/424 221/45 |
| 2015/0313425 A1* | 11/2015 | Thorén | A47K 10/427 221/1 |

* cited by examiner

*Primary Examiner* — Gene O Crawford
*Assistant Examiner* — Ayodeji T Ojofeitimi
(74) *Attorney, Agent, or Firm* — Taft Stettinius & Hollister LLP; Ryan O. White; Daniel J. Krieger

(57) ABSTRACT

A product dispensing apparatus for dispensing hygiene products. The product dispensing apparatus includes a housing having a back portion, a side portion coupled to the back portion, and a housing door movably coupled to the side portion. A product container is configured to hold a plurality of the hygiene products wherein the product container includes a support wall and side walls coupled to the support wall. The product container is rotatably coupled to the housing, and the product container is rotatable between a loading position and a dispensing position with respect to the housing. A product door is rotatably coupled to the product container and a trigger assembly is supported by the product container. A product delivery tray is rotatably supported by the side walls of the product container and extends through a slot in the support wall during rotation of the product delivery tray.

20 Claims, 10 Drawing Sheets

BULK LOADING FEMININE HYGIENE PRODUCT DISPENSER

FIELD OF THE DISCLOSURE

The present disclosure relates to a vending machine that dispenses hygiene products. More specifically, the present disclosure relates to a bulk loading vending machine that dispenses feminine hygiene products in response to activation of a trigger.

BACKGROUND OF THE DISCLOSURE

Different types of vending machines dispense hygiene products in response to a buyer depositing money at the machine, such as coinage or paper bills. Other types of vending machines dispense hygiene products in response to activation of a contact or non-contact sensor without the need to deposit any type of money. Such machines are often located in the restrooms of public or corporate buildings to dispense feminine hygiene products. The owners or proprietors of such facilities provide the feminine hygiene products without remuneration, since such products are considered to be essential and, as such, are provided free of charge.

In some facilities, where these hygiene product dispensers are located in low traffic areas, the dispensing machine does not require a large storage area for storing products. For instance, smaller restaurants and smaller schools do not require large capacity feminine hygiene product dispensers due to a lower demand for the products. Consequently, these types of reduced traffic facilities are not interested in purchasing large capacity dispensers due to the higher cost associated with such dispensers. What is needed therefore, is a hygiene product dispenser having a lower capacity that can be easily filled, but which still reduces the likelihood of an individual removing more products than is necessary.

SUMMARY

In one embodiment, there is provided a product dispensing apparatus for dispensing hygiene products. The product dispensing apparatus includes a housing having a back portion, a side portion coupled to the back portion, and a housing door movably coupled to the side portion. A product container is configured to hold a plurality of the hygiene products wherein the product container includes a support wall and side walls coupled to the support wall. The product container is rotatably coupled to the housing, and the product container is rotatable between a loading position and a dispensing position with respect to the housing. A product door is rotatably coupled to the product container and a trigger assembly is supported by the product container. A product delivery tray is rotatably supported by the side walls of the product container at a rotational axis, wherein the product delivery tray is rotatably coupled to the trigger assembly and the trigger assembly moves the delivery tray from a product receiving position to a product delivery position.

In some embodiments, the product dispensing apparatus includes wherein the support wall includes a slot and the product delivery tray moves through the slot when moved by the trigger assembly from the product receiving position to the product delivery position.

In some embodiments, the product dispensing apparatus includes wherein at least a portion of the product delivery tray extends through the slot in the product receiving positon.

In some embodiments, the product dispensing apparatus includes wherein the product container is configured to support at least one vertical row of hygiene products in the dispensing position.

In some embodiments, the product dispensing apparatus includes wherein the product delivery tray includes a product receiving portion defined by a first lip and a second lip, wherein the product receiving portion receives a single hygiene product from the at least one vertical row when in the product delivery tray is in product receiving position.

In some embodiments, the product dispensing apparatus includes wherein the product delivery tray includes a product blocking portion, wherein the product blocking portion contacts a lowest one of the hygiene products of the at least one vertical row when in the product delivery position.

In some embodiments, the product dispensing apparatus further includes a timer defining a delay period, wherein the timer is operatively connected to the product container and prevents the product delivery tray from moving from the product delivery position to the product receiving position until the delay period has elapsed.

In some embodiments, the product dispensing apparatus further includes wherein the trigger assembly is prevented from moving the delivery tray from the product delivery position to the product receiving position until the delay period has elapsed.

In some embodiments, the product dispensing apparatus includes wherein the timer includes a timing plate and a suction cup, wherein actuation of a trigger of the trigger assembly compresses the suction cup to the timing plate to set the delay period, and a release of the suction cup from the timing plate determines when the delay period has elapsed.

In some embodiments, the product dispensing apparatus includes wherein vertical movement of the trigger in a downward direction moves the delivery tray from the product receiving position to the product delivery position and vertical movement of the trigger in an upward direction does not move the delivery tray from the product delivery position to the product receiving position until the delay period has elapsed.

In another embodiment, there is provided a product module for a product dispensing apparatus to dispense hygiene products. The product module includes a product container configured to hold and dispense a plurality of the hygiene products. The product container includes a support wall and side walls coupled to the support wall, wherein the product container is configured to be rotatably coupled within the product dispensing apparatus, and the product container is rotatable between a loading position and a dispensing position. A product door is rotatably coupled to the product container and a trigger assembly is supported by the product container. A product delivery tray is rotatably supported by the side walls of the product container at a rotational axis, wherein the product delivery tray is rotatably coupled to the trigger assembly and the trigger assembly moves the delivery tray from a product receiving position to a product delivery position.

In some embodiments, the product module includes wherein the support wall includes a slot and the product delivery tray moves through the slot when moved by the trigger assembly from the product receiving position to the product delivery position.

In some embodiments, the product module includes wherein at least a portion of the product delivery tray extends through the slot in the product receiving positon.

In some embodiments, the product module includes wherein the product container is configured to support at least one vertical row of hygiene products in the dispensing position.

In some embodiments, the product module includes wherein the product delivery tray includes a product receiving portion defined by a first lip and a second lip, wherein the product receiving portion receives a single hygiene product from the at least one vertical row when the product delivery tray is in the product receiving position.

In some embodiments, the product module includes wherein the product delivery tray includes a product blocking portion, wherein the product blocking portion contacts a lowest one of the hygiene products of the at least one vertical row when in the product delivery position.

In some embodiments, the product module includes a timer defining a delay period, wherein the timer is operatively connected to the product container and prevents the product delivery tray from moving from the product delivery position to the product receiving position until the delay period has elapsed.

In some embodiments, the product module includes wherein the trigger assembly is prevented from moving the delivery tray from the product delivery position to the product receiving position until the delay period has elapsed.

In some embodiments, the product module includes wherein the timer includes a timing plate and a suction cup, wherein actuation of a trigger of the trigger assembly compresses the suction cup to the timing plate to set the delay period, and a release of the suction cup from the timing plate determines when the delay period has elapsed.

In some embodiments, the product module includes wherein vertical movement of the trigger in a downward direction moves delivery tray from the product receiving position to the product delivery position and vertical movement of the trigger in an upward direction does not move the delivery tray from the product delivery position to the product receiving position until the delay period has elapsed.

Further novel features and other aspects of the present invention will become apparent from the following detailed description and discussion.

BRIEF DESCRIPTION OF THE DRAWINGS

Referring particularly to the drawings for the purpose of illustration only and not limitation, there is illustrated as follows.

DETAILED DESCRIPTION OF THE EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

Figure 1:
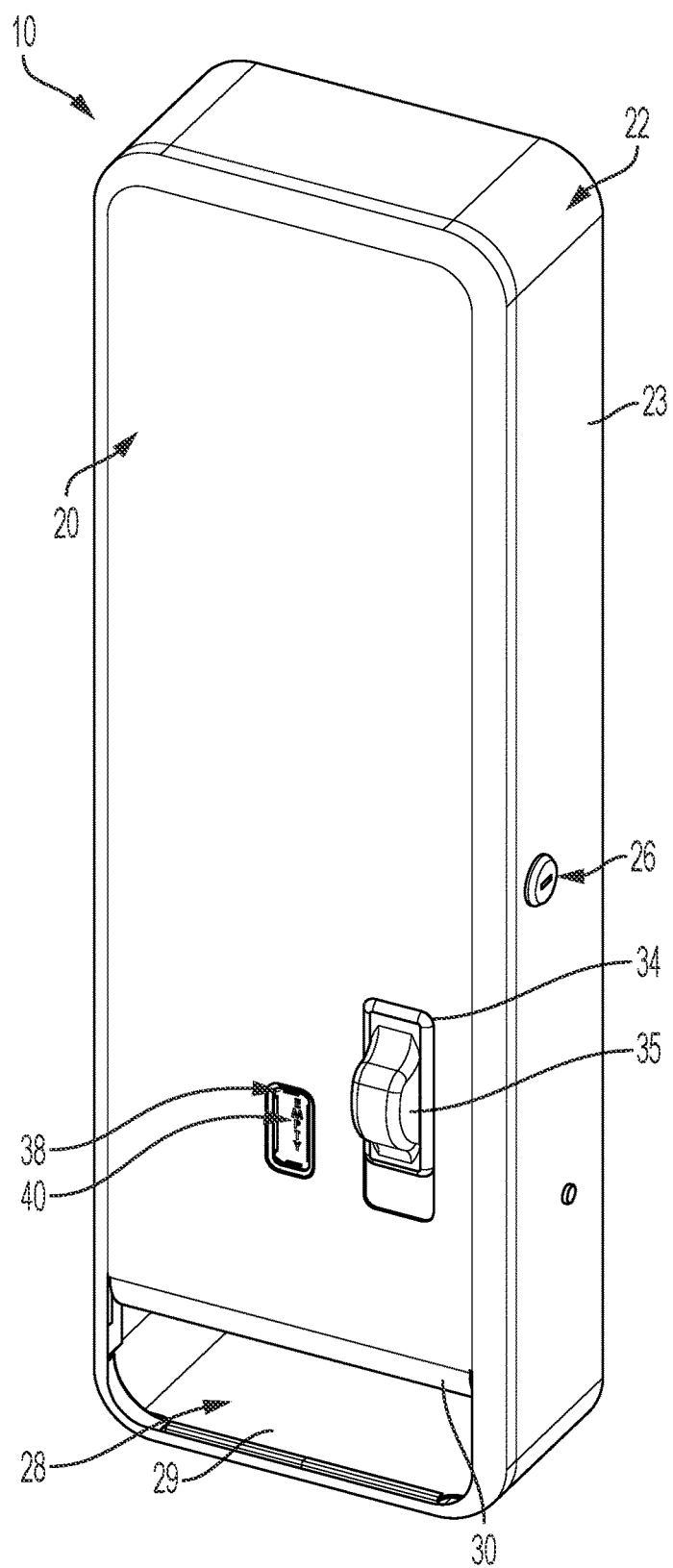
FIG. 1 illustrates an elevational perspective front view of a product dispenser in a closed condition.
Figure 2:
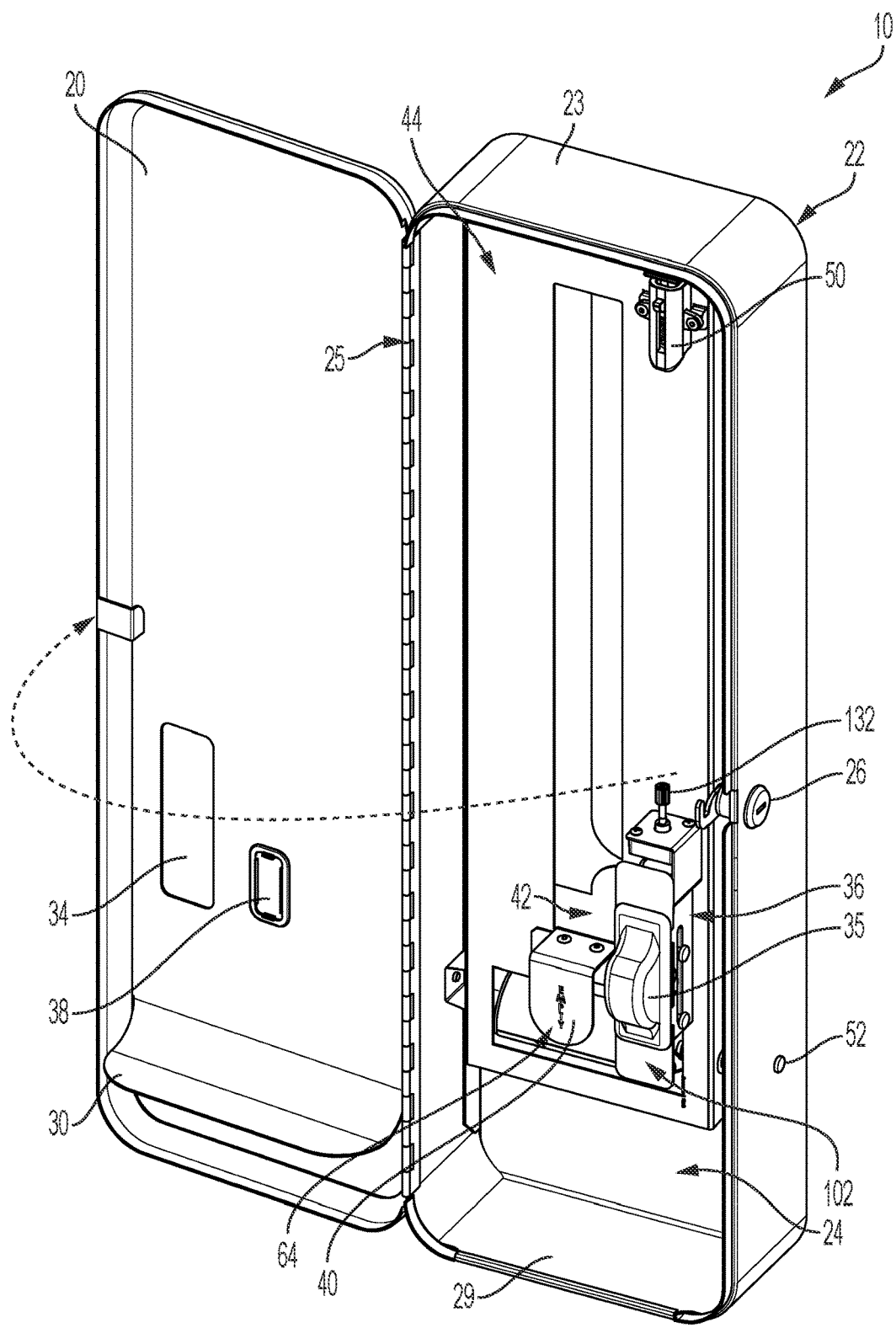
FIG. 2 illustrates an elevational perspective front view of a product dispenser with a door in an open position.

FIGS. 1 and 2 illustrate a feminine hygiene product dispensing apparatus 10. The apparatus 10 includes a front door 20 coupled to a cabinet or housing 22. In one embodiment, the housing 22 is a unitary single piece housing. In another embodiment, the housing includes side portion 23 coupled to a separate back wall 24. The front door 20 is hinged to the housing 22 with a hinge 25 to enable the door 20 to open when a lock 26 is unlocked. In other embodiments, a plurality of locks is included and can be located on side portions, a top portion, or bottom portion of the housing 22. The front door 20 defines a space 28 with the housing 22 which enables a user to remove a dispensed product from the apparatus 10. The housing 22 defines a tray 29. A guard 30 (see FIG. 2) is connected to an inside face of the door 20 which substantially prevents an individual from reaching into the apparatus to remove additional products, as opposed to taking products one by one in response to actuation of a trigger assembly 36.

The door 20 includes an opening 34, at which a trigger 35 of a trigger assembly 36 is located. A window 38 includes a transparent lens which is sufficiently transparent to enable a consumer to see an indicator or mark 40 (see FIG. 2) which indicates that the apparatus 10 is out of hygiene products and requires filling. In this embodiment, the word "Empty" is located on a face of a weight assembly 42. In one embodiment, the dispenser dispenses a product without requiring a payment or any other compensation, wherein the products are provided as a courtesy. In other embodiments, compensation is required including, coins, bills, credit cards, debit cards, and cryptocurrency.

A product module 44 includes a product container 45 having a front wall or support wall 46 and side walls 48. The product container 45 is configured to hold a plurality of hygiene products (not shown) which are arranged in one or more columns. In one embodiment, the hygiene products are feminine hygiene products, including tampons that are typically cylindrical having a length longer than a diameter of the tampon. Other products having other dimensions are contemplated. The products are stacked one upon another and the weight assembly 42 is placed on one or more products located at the top of a stack of hygiene product. The weight compresses the stack to insure proper dispensing and also includes the indicator 40.

Figure 3:
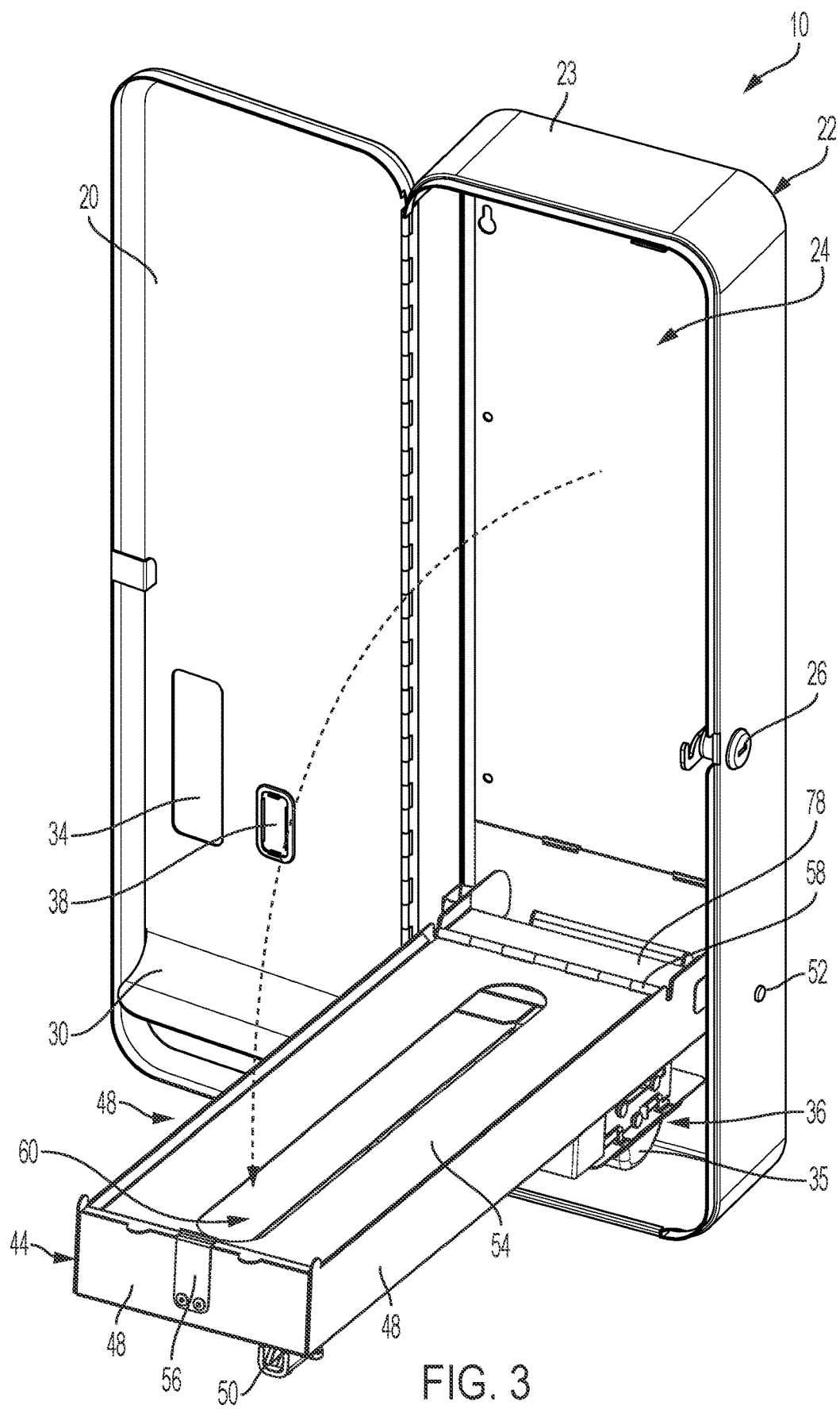
FIG. 3 illustrates an elevational perspective front view of a product dispenser in an open condition with a dispenser module in a lowered position and closed condition.

As seen in FIG. 2, the product module 44 is shown as being empty of product and ready to be filled with products for dispensing, When empty, the product weight assembly 42 is at its lowest position and the indicator 40 would be positioned to be seen through the window 38. A module release trigger 50 holds the product module in the illustrated upright positon of FIG. 2. To refill, the product module 44, the release trigger 50 is actuated to enable the product module 44 to be moved to a product loading position as illustrated in FIG. 3. Once released, the product module 44 is rotated about a module pivot 52 to the loading position in which the front wall 46, i.e. the support wall, is moved to a support position for supporting a plurality of hygiene products which are loaded into the module 44. In the support position, the product module 44, including the front wall 46, is generally inclined with respect to the back wall 24 to hold the hygiene products when being loaded.

Figure 4:
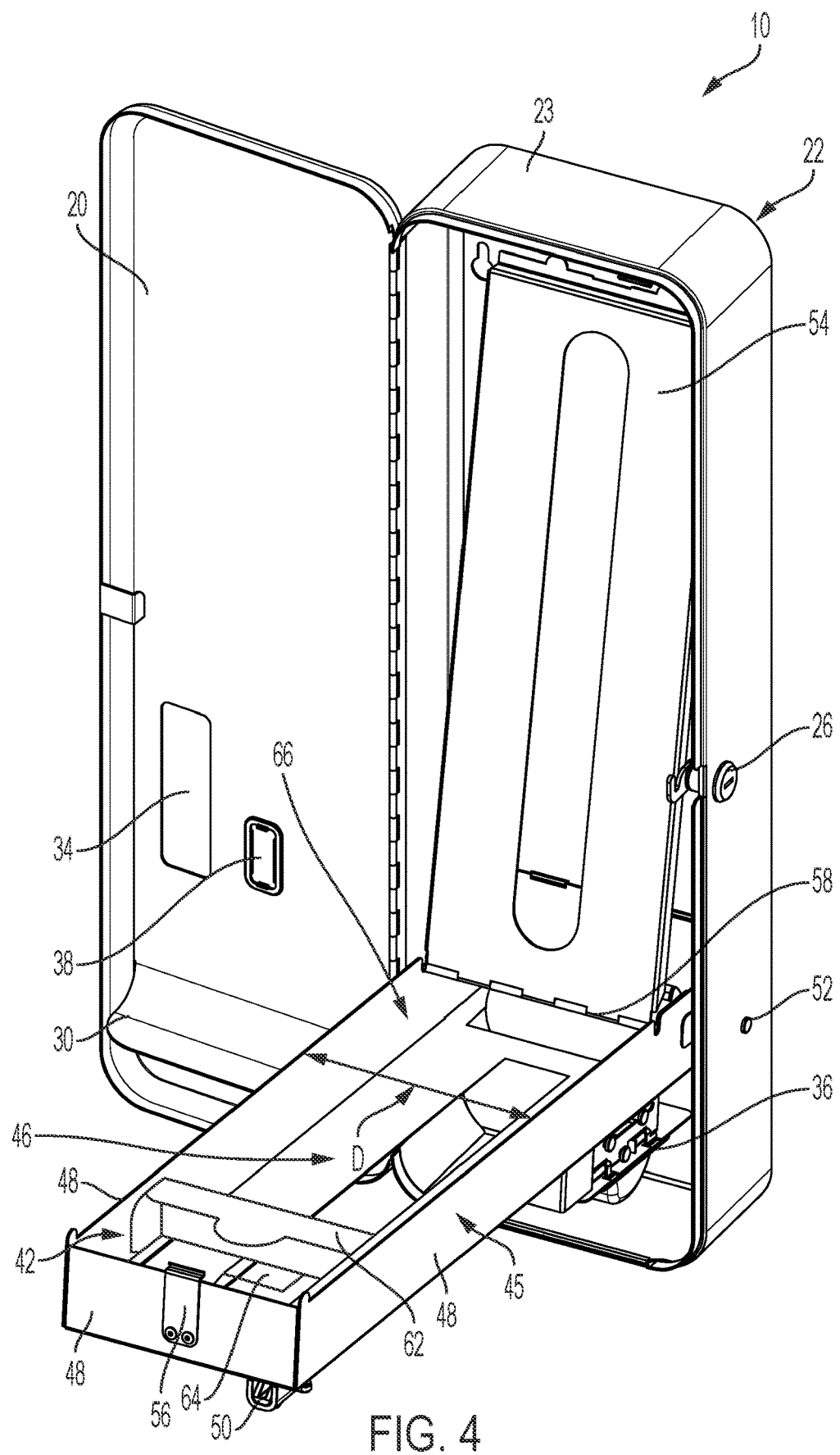
FIG. 4 illustrates an elevational perspective front view of a product dispenser in an open condition with a product module in a lowered position and an opened condition.
Figure 5:
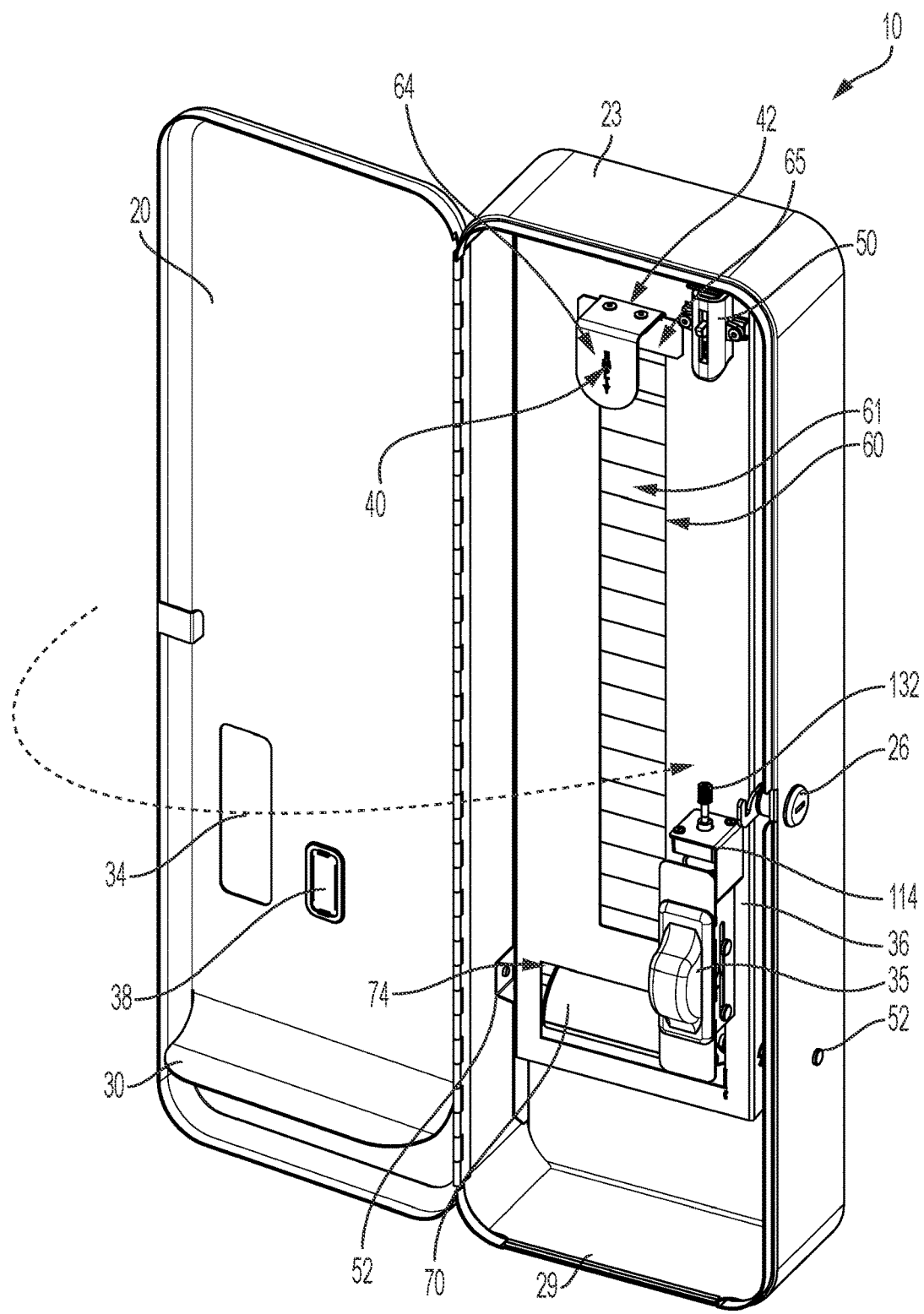
FIG. 5 illustrates an elevational perspective front view of a dispenser apparatus in an open condition with a product module in a raised position including hygiene products for dispensing.

To load products, a module door 54 is rotatably coupled to the product container 45 and is movable from a closed position of FIG. 3 to an open position of FIG. 4. A door catch 56, coupled to one of the side walls 48, is released and the module door 54 is rotated about a door hinge 58 coupled to two of the side walls 48. Once the module door 54 is opened, the weight assembly 42 is moved toward the door catch 56 to provide a storage area for hygiene products that rest on a surface of the support wall 46. In one embodiment, the support wall 46 defines an elongated aperture 60 though which stored hygiene products 61110 can be viewed, for instance, as seen in FIG. 5. In some embodiments, the weight assembly 42 includes a body 62 coupled to a handle 64 (see also FIG. 2 and FIG. 5) wherein a connection between the handle 64 and the body 62 is fixed. A weight plate 65, as seen in FIG. 5, is coupled to the handle 64 and is wider than the slot 60 such that the weight assembly 42 cannot be removed from the support wall 46, to substantially prevent removal or loss of the weight 42. The weight assembly 42 freely slides along the slot 60. In one embodiment, the weight plate 65 includes a sufficient mass to enable the weight assembly 42 to compress and hold the hygiene products to be dispensed.

Because the module door 54 opens sufficiently to expose a large portion or a complete portion of a storage area 66 defined by the support wall 46 and the side walls 48, hygiene products can be quickly loaded into the product module. Since the storage area 66, in at least one embodiment, does not include dividers or other alignment features, a plurality of hygiene products can be loaded at a time, i.e. bulk loaded, which reduces the time for filling the dispenser with products. In addition, a distance D between sidewalls 48 is selected to be a length of the product. When dispensing tampons for instance, the distance D is selected to enable product to be stacked generally parallel to the hinge 58 and as further illustrated in FIG. 5.

As shown in FIGS. 2, 3, and 4, the trigger assembly 36 is fixedly connected to the product module 44 and in one or more embodiments is fixedly connected to the support wall 46. For instance as seen in FIG. 4, rotation of the product module 44 to the loading position moves the trigger assembly 36 from the dispensing position of FIG. 2, since it is a part of and fixed to the module 44. Once the product module 44 is loaded as seen in FIG. 5, the module 44 and the trigger assembly 36 are returned to the dispensing position. The module 44 including the trigger assembly 36 are a single unit and if replacement or repair is required, the module 44 is replaceable as a unit such that the cabinet housing 22 and door 20 need not be changed.

Figure 6:
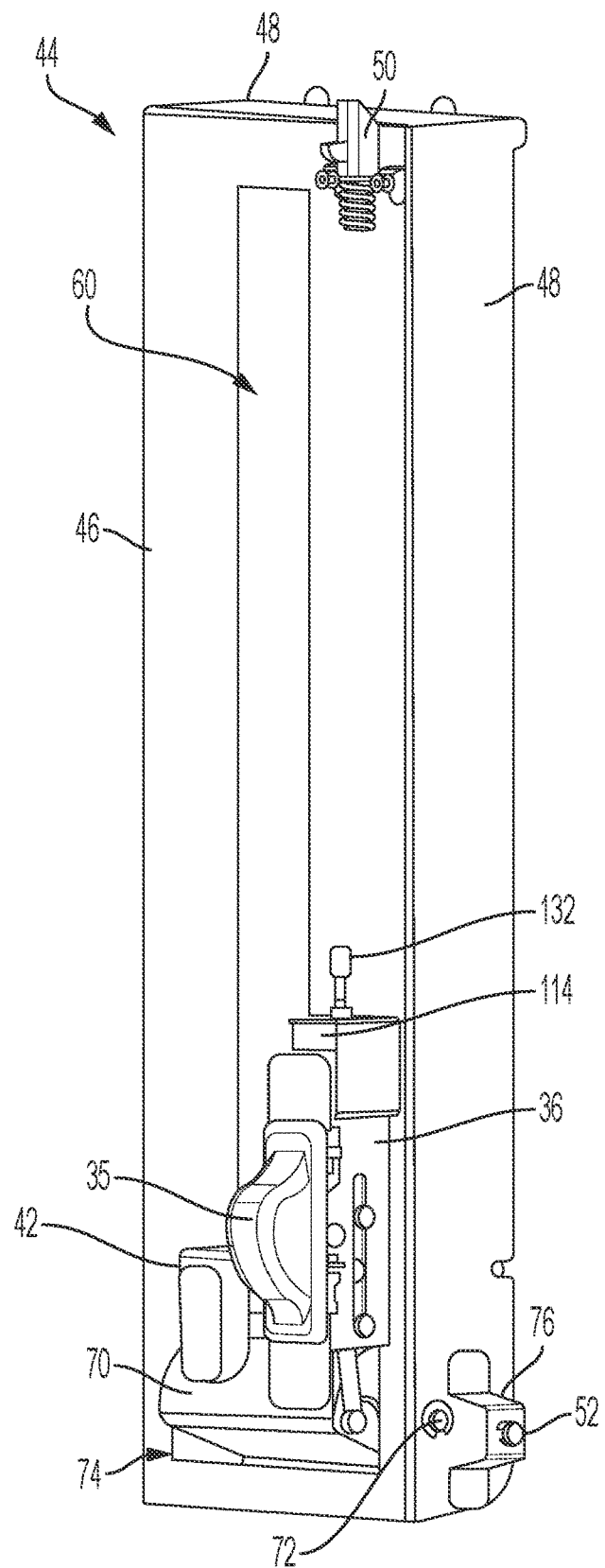
FIG. 6 illustrates an elevational perspective front view of a product module.

As seen in FIG. 5 and FIG. 6, the trigger assembly 36 is operatively connected to a product delivery tray 70, which is also operatively connected to the product module 44. Consequently, as the product module 44 is rotated about the module pivot 52 both the trigger assembly 36 and the product delivery tray 70 move with movement of the product module 44. When dispensing product and upon actuation of the trigger assembly 36, the product delivery tray 70 pivots about a delivery tray pivot 72, as seen in FIG. 6, to dispense product. To enable pivoting of the product delivery tray 70, the support wall 46 includes a tray slot 74 which is sized to enable the product delivery tray 70 to rotate for dispensing hygiene products. Module brackets 76, one of which is shown in FIG. 6, extend from opposed side walls 48 of the product module 44 to rotatably support the module 44.

Figure 7:
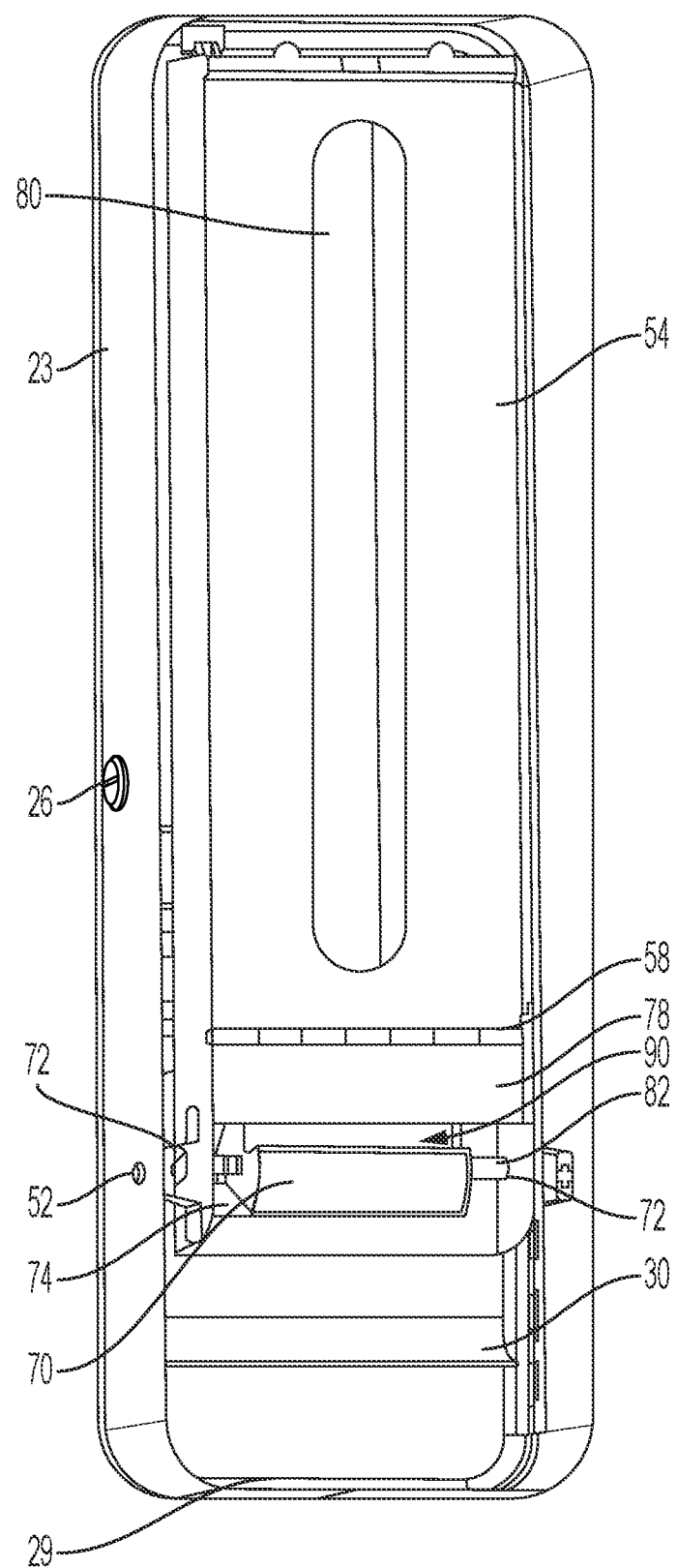
FIG. 7 illustrates an elevational perspective rear view of a product module enclosed by a portion of a product dispenser housing.

FIG. 7 illustrates an elevational rear perspective view of the product module 44 shown with the side portion 23 of the dispenser 10. The door hinge 58 is coupled to a hinge plate 78 which is fixedly connected to side walls 48 of the product module 44. In this way, the module door 54 rotates about an axis defined by the hinge 58 at the hinge plate 78. In one embodiment, the module door 54 includes a slot 80 to provide air flow within the storage area 66 for loading as well as dispensing product. Otherwise, without the slot 80, storing and dispensing of product can be impeded.

A delivery tray shaft 82 extends through the delivery tray 70 to define the tray pivot 72, i.e. a rotational axis for the delivery tray. In one embodiment, the delivery tray shaft 82 extends through the delivery tray 70 and includes ends coupled to opposed side walls 48 of the module 44. In other embodiments, the delivery tray shaft 82 includes two or more parts connecting opposed ends of the tray 70 to walls 48. The delivery tray shaft 70 is disposed adjacently to the delivery tray slot 74 such that a portion of the delivery tray 70 extends into the storage area 66 and another portion of the delivery tray 70 extends outwardly from the slot 70 toward the door 20. In this way, a product holder 90 of the delivery tray 70 is disposed beneath a stack or column of hygiene products stored in the module 44.

Figure 8:
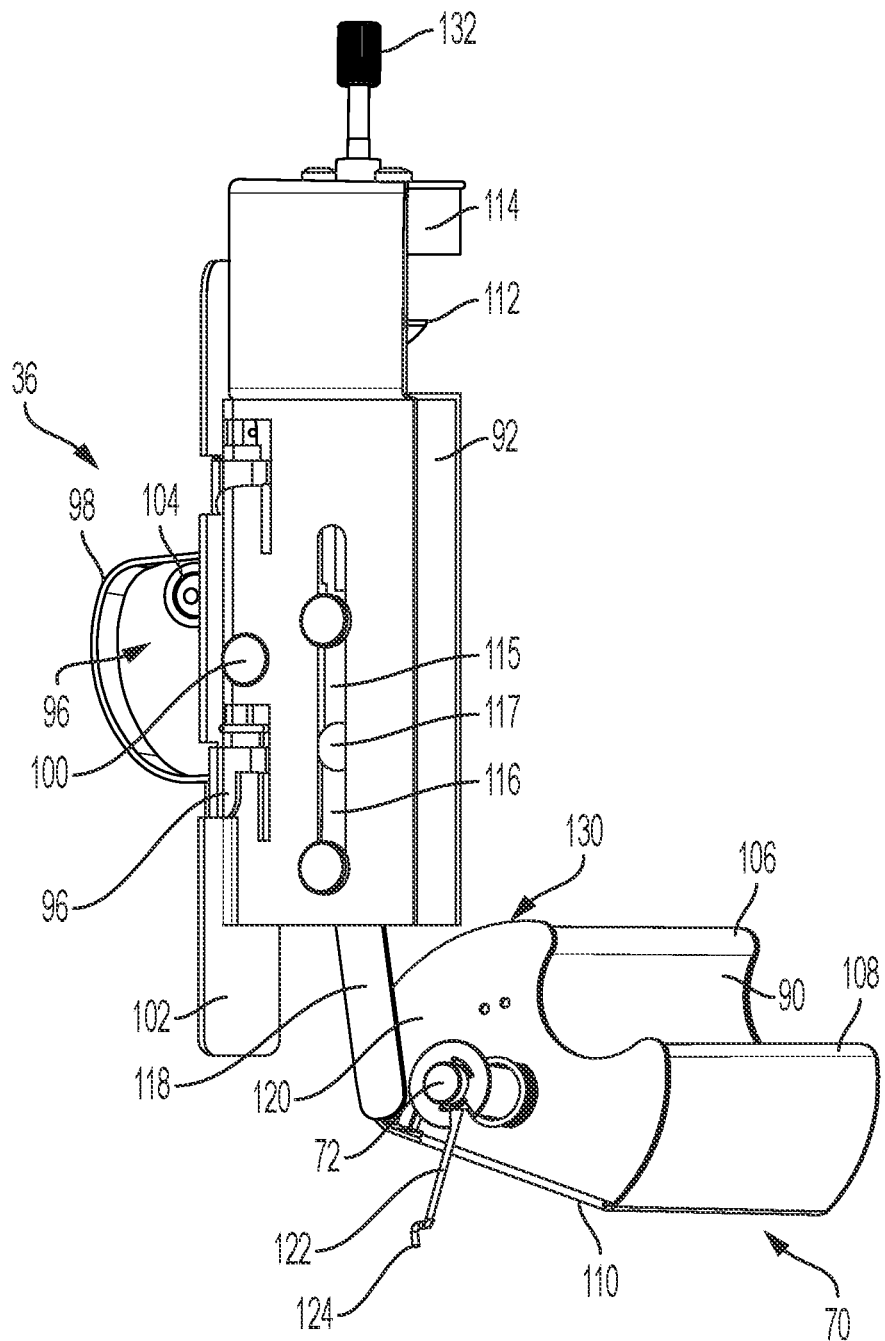
FIG. 8 illustrates a trigger assembly coupled to a delivery tray, positioned in a receiving position.
Figure 9:
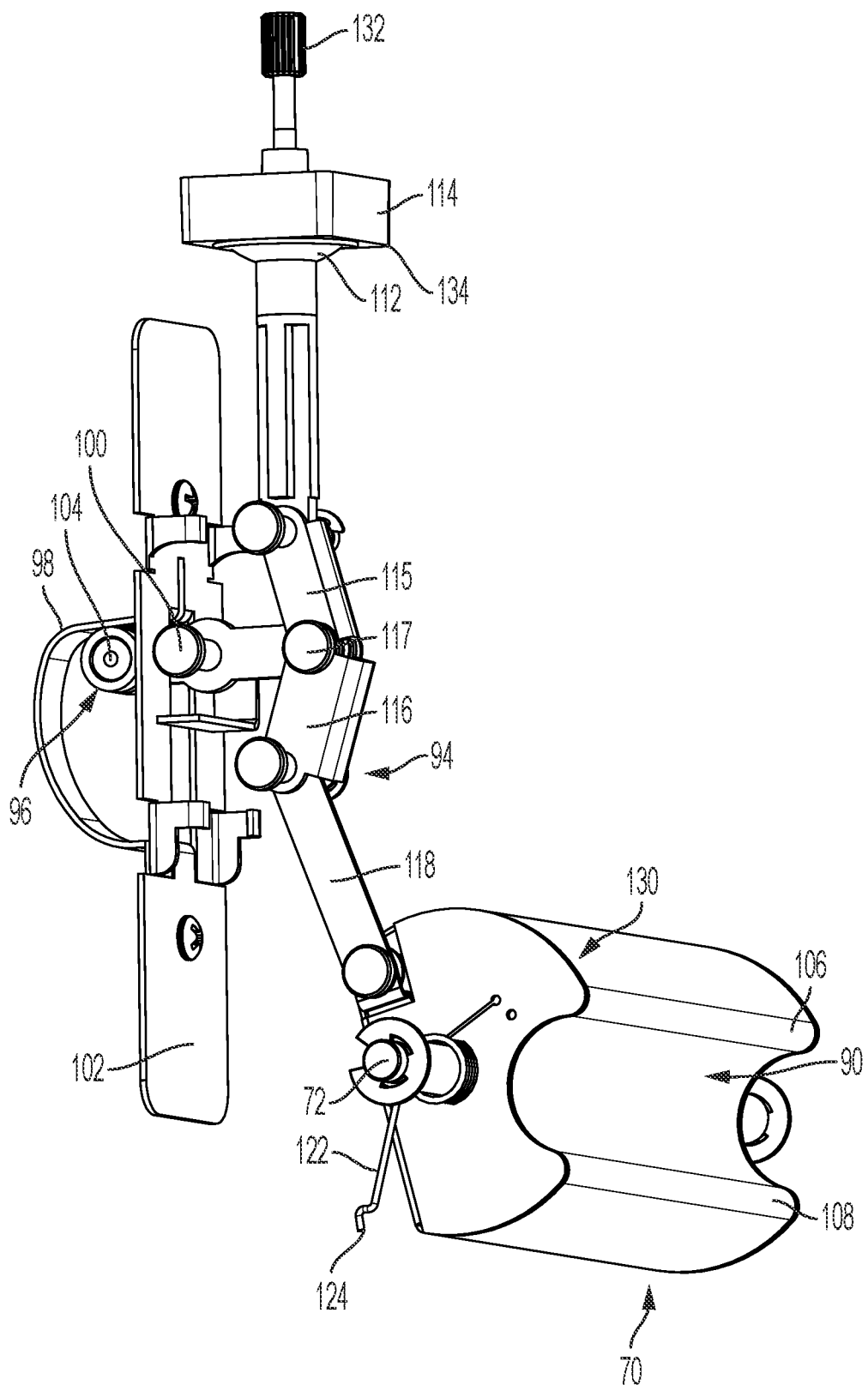
FIG. 9 illustrates a trigger assembly coupled to a delivery tray, positioned in a delivery position.

FIGS. 8 and 9 illustrates the trigger assembly 36 coupled to the delivery tray 70. In FIG. 8, the delivery tray 70 is positioned with the product holder 90 in a receiving positon for receiving a single product from the plurality of products stored in the product module 44. In FIG. 9, the delivery tray 70 is positioned in a dispensing position for dispensing the product located in the product holder 90. The trigger assembly 36 includes a housing 92 supporting a linkage 94 which is activated by a lever 96. A trigger support 98 (a trigger cover for the support 98 is not shown but can be seen in FIG. 1) moves one end of the lever 96 about a pivot 100 held for rotation by the housing 92. The trigger support 98 is fixedly connected to a trigger plate 102 which moves vertically in both a downward and an upward direction as illustrated. Downward movement of the trigger support 98 moves a first end 104 of the lever 96 about the pivot 100. This downward movement of the trigger support 98 also moves the trigger plate 102 in a downward direction. The trigger plate 102 is slidingly supported by the housing 92, which is fixedly connected to the module 44. Downward movement of the trigger support 98 moves the delivery tray 70 from a product receiving position of FIG. 8 to the product delivery position of FIG. 9.

The delivery tray 70 includes the product holder 90 which is located between a first lip 106 and a second lip 108 each of which extend upwardly from a base 110. The product holder 90 is configured to support and hold the hygiene product.

When the delivery tray 70 is in the product receiving position, a suction cup 112, coupled to the linkage 94, is spaced from a timing block 114. In this position, a first link 115 is rotatably coupled to a second link 116 and are generally aligned along a longitudinal axis. A second end 117 of the lever 96 is coupled to coupled ends of the first link 115 and second link 116. A first end of a third link 118 is coupled to the second link 116 and a second end of the third link 118 is rotatably coupled to a side 120 of the delivery tray 70. The delivery tray 70 is held in the receiving position of FIG. 8 by a resilient member or spring 122. A free end 124 of the spring 122 is held in tension by a stop on the module (not shown) to maintain the delivery tray 70 in the receiving position.

To deliver a product to a user, the user moves the trigger 35 in a downward direction. In response the trigger support 98 moves in a downward direction, as illustrated in FIG. 9, which in turn moves the second end 117 of lever 96 in an upward direction which moves links 114 and 116 out of longitudinal alignment which pulls third link 118 upwardly. Upward movement of the third link 118 rotates the delivery tray about the shaft 82. The delivery tray 70 rotates in a clockwise direction, as illustrated, to drop the product into the space 28 of the dispenser. In this position, a blocking portion 130 of the delivery tray 70 also moved in an upward direction when comparted to its position in FIG. 8. The blocking portion 130 is now located at the bottom of a stack or vertical column of products. This location of the blocking portion 130 prevents product from being dispensed.

An air flow screw 132 coupled to the timing block 114 determines a delay period in which another product cannot be dispensed. The delay period is determined by how long the suction cup 112 remains in contact with the timing block 114. During this period of contact, movement of the trigger in either the upward or downward position does not move the lever 96 about pivot 100. The trigger is free to move in the upward direction, but does not dislodge the lever 96 from its position maintained by contact of the suction cup 112 to the timing block 114.

Adjustment of the air flow screw 132 changes a volume of air within the timing block 114. An aperture (not shown), in a bottom surface 134 of the timing block, is located at an interface between the bottom surface 134 and the suction cup 112. Adjustment of the screw 132 changes the time of the delay period. Once the delay period has elapsed, the delivery tray 70 returns to the position of FIG. 8 due to the tension of spring 124. See also issued U.S. Pat. No. 11,769,363 the entirety of which is incorporated by reference herein in its entirety.

Figure 10C:
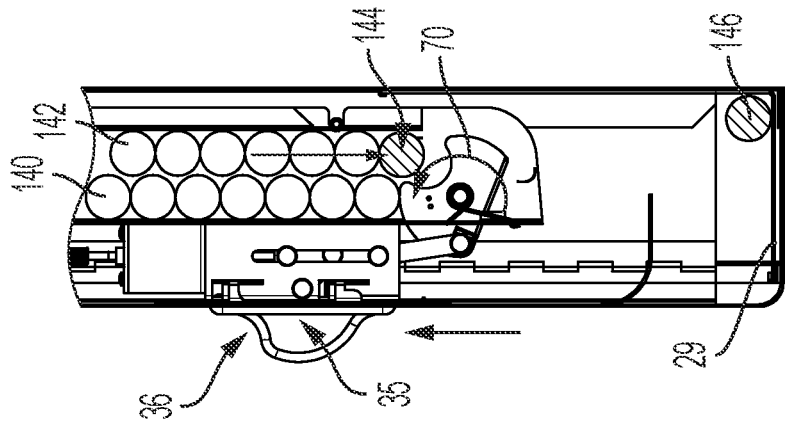
FIGS. 10A-C illustrate dispensing of a hygiene product with the delivery tray in three positions.
Figure 10B:
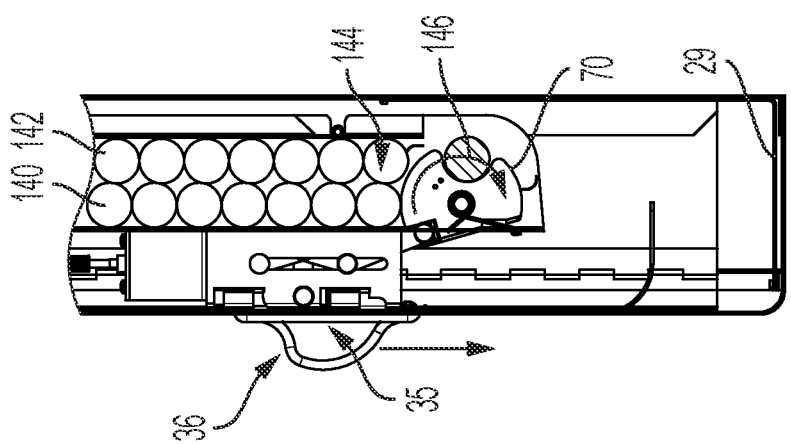
Figure 10A:
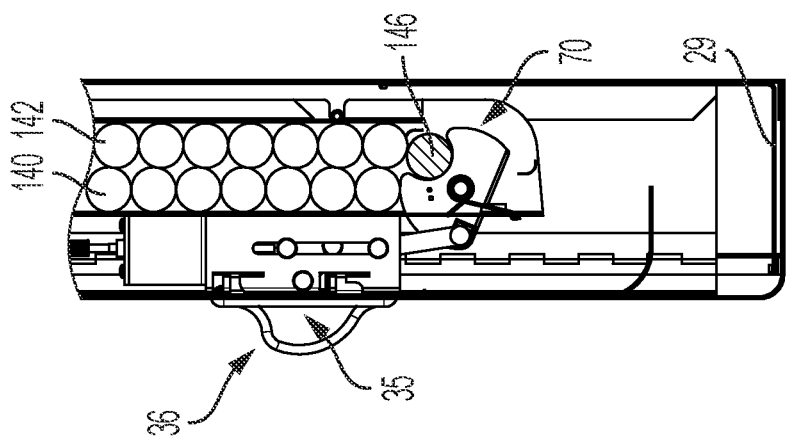

FIGS. 10A-10C illustrate a dispensing sequence of a hygiene product with the delivery tray 70. In FIG. 10A, the product module 44 supports a first column 140 and a second column 142 of hygiene products, for instance tampons which are shown. A bottommost product 144 is supported by the blocking portion 130 and the product holder 90 receives a product 146 of the second column 144. In FIG. 10B, upon actuation of the trigger, product 146 is dispensed from column 142 to the open space 28 and onto the tray 29 of FIG. 10C Upon release of the suction cup 112 from the timing block 114, the product holder 90 return to the position of FIG. 10A.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. A product dispensing apparatus for dispensing hygiene products comprising:
   a housing including a back portion, a side portion coupled to the back portion, and a housing door movably coupled to the side portion;
   a product container configured to hold a plurality of the hygiene products, the product container including a support wall and side walls coupled to the support wall, wherein the product container is rotatably coupled to the housing, and the product container is rotatable between a loading position and a dispensing position with respect to the housing;
   a product door rotatably coupled to the product container;
   a trigger assembly supported by the product container; and
   a product delivery tray rotatably supported by the side walls of the product container at a rotational axis, wherein the product delivery tray is rotatably coupled to the trigger assembly and the trigger assembly moves the delivery tray from a product receiving position to a product delivery position.

2. The product dispensing apparatus of claim 1, wherein the support wall includes a slot and the product delivery tray moves through the slot when moved by the trigger assembly from the product receiving position to the product delivery position.

3. The product dispensing apparatus of claim 2, wherein at least a portion of the product delivery tray extends through the slot in the product receiving positon.

4. The product dispensing apparatus of claim 3 wherein the product container is configured to support at least one vertical row of hygiene products in the dispensing position.

5. The product dispensing apparatus of claim 4 wherein the product delivery tray includes a product receiving portion defined by a first lip and a second lip, wherein the product receiving portion receives a single hygiene product from the at least one vertical row when in the product delivery tray is in product receiving position.

6. The product dispensing apparatus of claim 5 wherein the product delivery tray includes a product blocking portion, wherein the product blocking portion contacts a lowest one of the hygiene products of the at least one vertical row when in the product delivery position.

7. The product dispensing apparatus of claim 6 further comprising a timer defining a delay period, wherein the timer is operatively connected to the product container and prevents the product delivery tray from moving from the product delivery position to the product receiving position until the delay period has elapsed.

8. The product dispensing apparatus of claim 7 wherein the trigger assembly is prevented from moving the delivery tray from the product delivery position to the product receiving position until the delay period has elapsed.

9. The product dispensing apparatus of claim 8 wherein the timer includes a timing plate and a suction cup, wherein actuation of a trigger of the trigger assembly compresses the suction cup to the timing plate to set the delay period, and a release of the suction cup from the timing plate determines when the delay period has elapsed.

10. The product dispensing apparatus of claim 9 wherein vertical movement of the trigger in a downward direction moves the delivery tray from the product receiving position to the product delivery position and vertical movement of the trigger in an upward direction does not move the delivery tray from the product delivery position to the product receiving position until the delay period has elapsed.

11. A product module for a product dispensing apparatus for dispensing hygiene product, the product module comprising:
- a product container configured to hold and dispense a plurality the hygiene products, the product container including a support wall and side walls coupled to the support wall, wherein the product container is configured to be rotatably coupled within the product dispensing apparatus, and the product container is rotatable between a loading position and a dispensing position;
- a product door rotatably coupled to the product container;
- a trigger assembly supported by the product container; and
- a product delivery tray rotatably supported by the side walls of the product container at a rotational axis, wherein the product delivery tray is rotatably coupled to the trigger assembly and the trigger assembly moves the delivery tray from a product receiving position to a product delivery position.

12. The product module of claim 11, wherein the support wall includes a slot and the product delivery tray moves through the slot when moved by the trigger assembly from the product receiving position to the product delivery position.

13. The product module of claim 12, wherein at least a portion of the product delivery tray extends through the slot in the product receiving positon.

14. The product module of claim 13 wherein the product container is configured to support at least one vertical row of hygiene products in the dispensing position.

15. The product module of claim 14 wherein the product delivery tray includes a product receiving portion defined by a first lip and a second lip, wherein the product receiving portion receives a single hygiene product from the at least one vertical row when the product delivery tray is in the product receiving position.

16. The product module of claim 15 wherein the product delivery tray includes a product blocking portion, wherein the product blocking portion contacts a lowest one of the hygiene products of the at least one vertical row when in the product delivery position.

17. The product module of claim 16 further comprising a timer defining a delay period, wherein the timer is operatively connected to the product container and prevents the product delivery tray from moving from the product delivery position to the product receiving position until the delay period has elapsed.

18. The product module of claim 17 wherein the trigger assembly is prevented from moving the delivery tray from the product delivery position to the product receiving position until the delay period has elapsed.

19. The product module of claim 18 wherein the timer includes a timing plate and a suction cup, wherein actuation of a trigger of the trigger assembly compresses the suction cup to the timing plate to set the delay period, and a release of the suction cup from the timing plate determines when the delay period has elapsed.

20. The product module of claim 19 wherein vertical movement of the trigger in a downward direction moves delivery tray from the product receiving position to the product delivery position and vertical movement of the trigger in an upward direction does not move the delivery tray from the product delivery position to the product receiving position until the delay period has elapsed.

* * * * *